United States Patent
Brennan

[19]

[11] Patent Number: 5,931,852
[45] Date of Patent: Aug. 3, 1999

[54] NOSE AIRWAY DEVICE

[76] Inventor: H. George Brennan, 1441 Avocado Ave., Ste. 204, Newport Beach, Calif. 92660

[21] Appl. No.: 08/871,565

[22] Filed: Jun. 4, 1997

[51] Int. Cl.$^6$ .................................................. A61B 17/00
[52] U.S. Cl. .............................................................. 606/199
[58] Field of Search ............................... 606/1, 198, 199, 606/201, 204.45; 600/220; 128/200

[56] References Cited

U.S. PATENT DOCUMENTS

| 1,034,566 | 8/1912 | Barratt | 606/199 |
| 1,069,459 | 8/1913 | Myles | 606/199 |

FOREIGN PATENT DOCUMENTS

| 0768488 | 2/1957 | United Kingdom | 606/199 |

*Primary Examiner*—Michael Buiz
*Assistant Examiner*—William Lewis
*Attorney, Agent, or Firm*—Michael G. Petit

[57] ABSTRACT

A device for establishing and maintaining an airway through the nasal passages. The device is a clip of unitary construction with a proximal "UU" shaped dilating portion adapted to be inserted within the nostrils; the "U's" being connected to one another medially by an elastically deformable extension portion, the extension portion being two straight parallel strips, one end of the strips being integral with the dilating portion and the opposing end of the strip integral with an arcuate septum attachment portion. The septum attachment portion spaces the distal ends of the strips of the extension portion so that the strips straddle and gently squeeze the nasal septum. The device provides maximum air flow through the nostrils. The device is attached to the nose by means of the distal elastically deformable septum attachment portion which is adapted to anatomically conform to and releasably engage the inferior margin of the nasal septum. The extension portion supports and stabilizes the proximal dilating portion within the nose. The length of the extension portion limits the distance the dilating portion extends within the nostrils and presents smooth, parallel flat septum contacting surfaces which press against and are stabilized by the opposing interior walls of the nasal septum. The proximal dilating portion of the device consists of two "U" shaped strips, each strip being affixed to a proximal open end of the "U" shaped extension portion and at right angles to the plane of the extension portion. The dilating portion presents a smooth outer tissue-contacting surface which urges against the inner surface of the walls of the nostrils forcing them outwardly. The tissue-contacting surface may include a medicament dispensing coating.

11 Claims, 2 Drawing Sheets

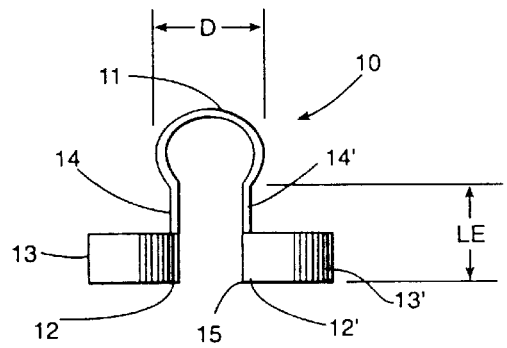
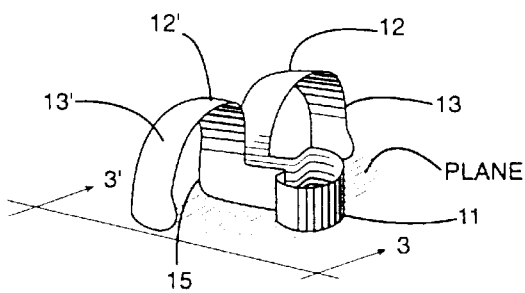
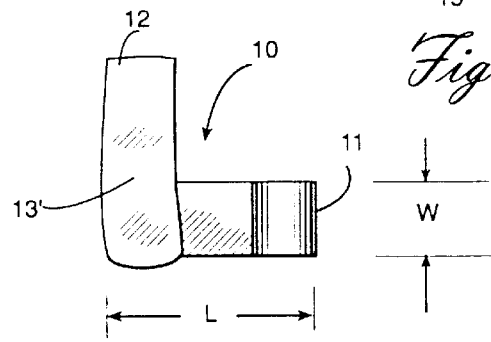
Figure 1
Figure 2
Figure 3
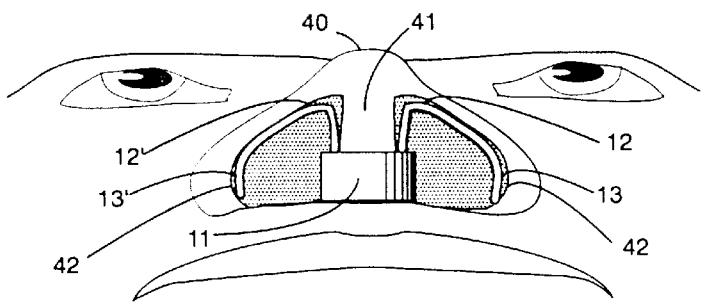
Figure 4
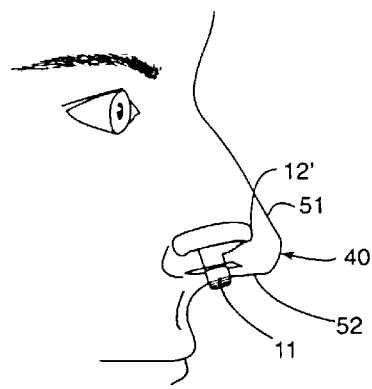
Figure 5

NOSE AIRWAY DEVICE

BACKGROUND OF THE INVENTION

1. Field of the Invention

This invention relates to a device adapted for temporary insertion within the nose for establishing and/or maintaining an airway through the nasal passages and delivering medicament thereinto.

2. Description of the Prior Art

Various forms of nasal airway devices are known in the art. Examples of such devices are disclosed in the following U.S. Pat. Nos. 851,048; 513,458, 4,414,977; 4,201,207; 2,515,756; 1,255,578; 1,481,581; 1,597,331; 1,672,591; 1,709,740; 1,135,675; 1,014,076; 1,014,758; 1,077,574 and British Patent GB0768488; British Patent 4,148; Italian Patent IT0490828 and French Patent 7807130. While most of these devices provide a means for dilating the nostrils and maintaining an airway permitting improved air flow therethrough, each has limitations producing less than optimum air flow or discomfort which prevents the device from being used for a prolonged period of time. Many devices are unsatisfactory due to non-unitary construction which can result in situ disintegration of the device and possible aspiration of a fragment of the device. The above devices do not have or teach the structural and functional features of the present invention described below which, in combination, enable the device to perform the intended function in a manner which is superior to the prior art devices.

Transdermal drug delivery devices and medically implantable devices which include an outer tissue contacting layer adapted to dispense drugs are known in the art. Examples of medicament dispensing coatings suitable for medical devices are described in the following U.S. Pat. Nos. 5,217,493; 5,567,495; 4,846,844; 4,952,419; 4,749,585; 4,879,135; 4,895,566; 4,915,694; 4,917,686 and 5,013,306. None of the foregoing patents teach a device wherein the tissue-contacting medicament dispensing portion of the device is adapted to intimately contact the inner surface of the nasal passage.

SUMMARY OF THE INVENTION

It is a primary object of this invention to provide a device adapted to be comfortably attached to a person's nose, thereafter being operable for increasing the flow of air through the nasal passages during periods of physical activity requiring high oxygen demand or increased ventilation.

It is another object of this invention to provide a device meeting the above objective and further having unitary construction and which includes a means for controlling and/or limiting the projection of the device into the nostrils while preventing the device from dislodging and being ejected from the nostril.

It is another object of this invention to provide a device which meets the objects stated above and which can be easily and inexpensively manufactured by injection molding from an inexpensive hypoallergenic plastic composite, copolymer or elastomer coated plastic in a variety of sizes.

It is yet a further object of this invention to provide a device as above which compensates for a deviated septum or nasal obstruction to enhance air flow through the effected nasal passages.

It is yet another object of the invention to provide a device adapted to be comfortably attached to the nose for extended sleep periods which is useful for reducing snoring.

It is yet a further object of this invention to provide a device for delivering a medicament to the respiration passages.

The above objects and advantages of the present invention are accomplished by the present device. The proximal dilating portion of the device comprises two "U" shaped surfaces adapted to be inserted into the nostrils. The dilating portion of the device is inter-connected by means of a bridging "U" shaped extension portion. The extension portion is a generally "U" shaped having a semicylindrical wall with an inner circumferential surface which is contoured to anatomically and snugly conform to the inferior (most distal) margin of the nasal septum. Thus, overall the device is generally "U" shaped, more or less resembling a cotter pin when viewed in front elevation and "U=U" shaped when the proximal portion is viewed end on from the top. The bifurcated extension portion comprises two identical substantially planar parallel strips oriented with their flat surfaces in parallel planes and connected to one another by the semicylindrical distal septum attachment portion. The symmetrical dilating portion is contoured to anatomically conform to the respective contours of the anterior inner surface of the nostrils.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

BRIEF DESCRIPTION OF THE DRAWINGS

FIG. 1 is a front elevational view of the present invention.

FIG. 2 is a perspective view of the device shown in FIG. 1.

FIG. 3 is a side view of the device of FIG. 2 viewed in the direction of line 3—3'.

FIG. 4 is a perspective inferior view of the device in accordance with the present invention positioned when the device is positioned within the nose of a person.

FIG. 5 is a schematic lateral view of the device positioned within the nose which has been partially cut-a-way for illustration.

DESCRIPTION OF THE PREFERRED EMBODIMENTS

Figure 6:
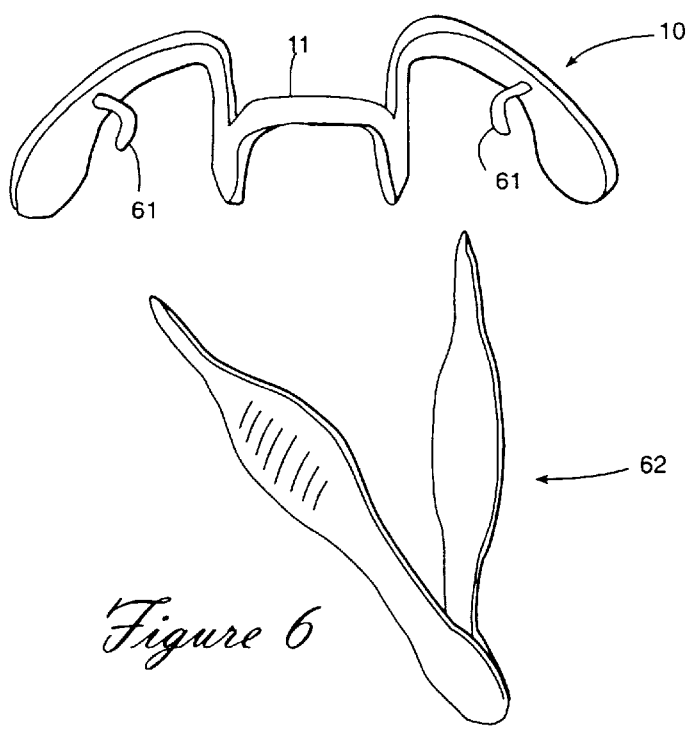
FIG. 6 is a perspective view of an embodiment of the invention having gripping pins adapted for facilitating instrument assisted insertion of the device into the nose.

The device 10, shown in front (anterior) elevational view in FIG. 1, is a unitary strip of elastically deformable material, preferably hypoallergenic, elastomer shaped to form a symmetrical 3-dimensional structure as generally shown in FIG. 2. The device is bifurcated and symmetrically disposed in structure with respect to the medial septum attachment portion 11. The septum attachment portion 11 is a semi-cylindrical arcuate distal coterminous for the inferior or distal end of the extension portion 14 and 14' of the device, connecting the tines 14 and 14' of the extension portion to one another and having an inner diameter D. The extension portion consists of tines 14 and 14' and extends proximally, away from the septum attachment portion a distance L, the proximal terminus of the extension portions 14, 14' being shown at 15. The dilating portion consists of two "U" shaped projections projecting anteriorly on a plane at right angles to the extension portion 14, to gracefully and arcuately curve laterally outward and posteriorly to form smooth, anatomically conforming tissue-contacting surfaces 13 and 13' which are mirror images of each other. The extension portion 14 and 14' preferably be a length L between ½ inch and 1 inch. The width W of the device 10 is substantially uniform throughout the device and preferably in the range of ⅛–⁵⁄₁₆ inches. The thickness of the device is also substantially uniform throughout and preferably less than ¹⁄₁₆ of an inch.

The device may be positioned within the nose 40 (FIG. 4) by inserting the proximal end 15 of the device 10 into the nasal air passages 42 and advanced by applying pressure on the distal opposing end until the distal septum attachment portion 11 is in contact with the inferior margin of the nasal septum 41. At this point, the proximal end 15 of the device 10 can be advanced no further into the nasal passages 42 and the anatomically conforming tissue-contacting surfaces 13 and 13' comprising the dilating portion press laterally against the anterior and lateral wall of the nasal passage to dilate the passage and maintain an airway therethrough.

The above described embodiment is shown in FIG. 5 wherein the device is seen to be comfortable positioned within the (partially sectioned) nose 40 of the patient. The surfaces 13 and 13' elastically urge outward to press laterally outward against the wall of the nasal passage and provide a smooth, non-irritating tissue-contacting surface for comfort. The anterior projection 12' of the dilating portion is shown facing the front or anterior portion 51 of the nose 40 and the septum attachment portion 11 is releasably attached to the inferior margin 41 of the nasal septum by medially directed elastic restorative forces.

Figure 7:
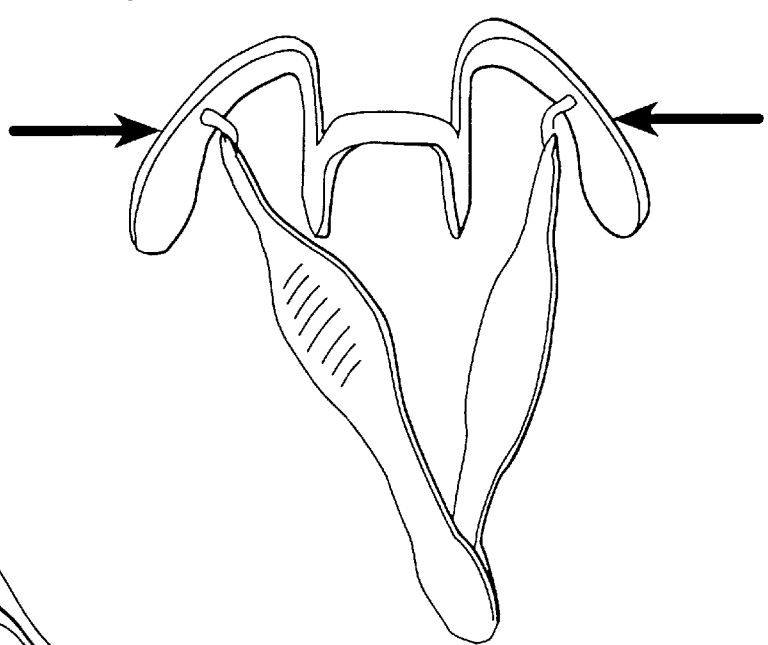
FIG. 7 shows the cooperative functional relationship between the insertion instrument and the device of FIG. 6 prior to insertion of the device into the nose.
Figure 8:
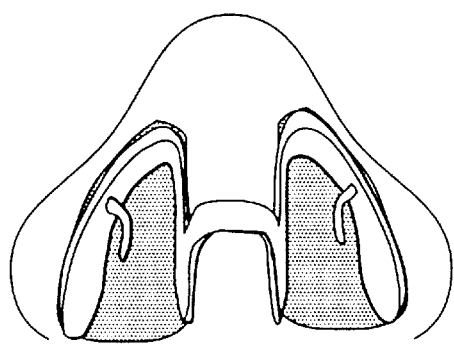
FIG. 8 is a elevational view of the device of FIG. 6 looking upward into the nose with the device properly positioned for operation.

FIG. 6 is a perspective view of an embodiment of the invention including gripping pins 61 adapted to be grasped by an instrument 62 for facilitating instrument assisted insertion of the device 10 into the nose. FIG. 7 shows the cooperative functional relationship between the insertion instrument 62 and device 10 prior to insertion of the device into the nose. The tines 14 and 14' of the extension portion of the device are urged toward one another in the direction indicated by the broad arrows in FIG. 7 and the proximal end 15 inserted into the person's anterior nasal passages and advanced thereinto by means of the instrument 62. When the pressure exerted by the instrument 62 on the pins 61 is released, the tines of the extension portion bear against the lateral tissue surfaces of the medial nasal septum to stabilize the while the proximal arcuate tissue-contacting surfaces of the dilating portion buttress a portion of the inner perimeter of the nasal passages, urging the tissue in contact therewith radially, outward to create and maintain symmetrically disposed open nasal airways. FIG. 8 is an elevational view looking upward into the nose 40 showing the device 10 properly positioned in accordance with this invention for maintaining an open airway within the nose. Medicament saturated dispensing pads 81 may be affixed to the inner surface 82 of the dilating portion of the device to release a volatile medicament contained therein to be entranced in the air stream and delivered to tissues leaving the resuscitator tract. The tissue-contacting surface 13 may be open cell and permeated with a medicament or the material comprising the device may be porous.

Alternatively, a thin film of silicone oil or a hydrogel or silicone gel coating containing a releasable medicament may be applied to the tissue-contacting surface of the device. Appropriate medicaments include, for example, antibiotics, steroids and volatile compositions exhibiting a therapeutic effect.

While particular embodiments of the present invention have been illustrated and described, it would be obvious to those skilled in the art that various other changes and modifications can be made without departing from the spirit and scope of the invention. For example, the device 10 is stabilized within the nose by contact with the lateral walls of the nasal septum and the interior surface of the nostrils. Accordingly, it may be used for correcting a deviated septum. It is therefore intended to cover in the appended claims all such changes and modifications that are within the scope of this invention.

What I claim is:

1. A device adapted for attachment to a person's nose for improving and/or maintaining an airway through the nasal passage of the nose, said device comprising:

(a) a dilating portion comprising two substantially U-shaped strips of an elastically deformable biocompatible material, said substantially U-shaped strips lying substantially in a first plane and being mirror images of one another and having a substantially uniform width and a smooth outer, tissue-contacting surface; and (b) an extension portion integral with said dilating portion comprising two straight strips of said elastically deformable biocompatible material having a length and said substantially uniform width, each of said two straight strips having a proximal end integral with one of the two U-shaped strips, a distal end, and an outer septum-contacting surface which is coplanar with at least a portion of said tissue-contacting surface of said U-shaped strip integral therewith; and (c) a septum attachment portion comprising a substantially arcuate strip of said elastically deformable material having said substantially uniform width, said substantially arcuate strip having two parallel straight edges, each straight edge being integral with a distal end of one of said straight strips comprising the extension portion wherein said two straight strips and said arcuate strip lie in a second plane which is orthogonal to said first plane.

2. The device of claim 1 wherein said length of said extension portion is between 0.5 and 1.0 inch.

3. The device of claim 2 wherein said width is between ⅛ and ⁵⁄₁₆ inch.

4. The device of claim 2 wherein said dilating portion further comprises a medicament dispensing reservoir affixed thereto.

5. The device of claim 1 wherein said width is between ⅛ and ⁵⁄₁₆ inch.

6. The device of claim 1 wherein said dilating portion further comprises a medicament dispensing reservoir affixed thereto.

7. The device of claim 1 wherein said tissue-contacting surface of said dilating portion is open-cell and permeated with a medicament.

8. The device of claim 1 wherein said material is porous.

9. The device of claim 1 wherein said tissue-contacting surface of said dilating portion further includes a thin film of silicone oil containing a medicament.

10. The device of claim 1 wherein said tissue-contacting surface of said dilating portion further includes a thin film of hydrogel coating containing a medicament.

11. The device of claim 1 wherein said tissue-contacting surface of said dilating portion further includes a thin film of silicone gel containing a medicament.

* * * * *